(12) United States Patent
Simon (10) Patent No.: US 7,282,046 B2
(45) Date of Patent: Oct. 16, 2007

(54) GLAUCOMA TREATMENT METHOD

(75) Inventor: Gabriel Simon, Madrid (ES)

(73) Assignee: Peter M. Adams, Doug P. Adams, and John Sullivan, Collectively as the Stockholder Representative Committee, San Jose, CA (US), on Behalf of the Participating Rights Holders of Solx, Inc.

( * ) Notice: Subject to any disclaimer, the term of this patent is extended or adjusted under 35 U.S.C. 154(b) by 153 days.

(21) Appl. No.: 11/041,715

(22) Filed: Jan. 24, 2005

(65) Prior Publication Data

US 2005/0165385 A1 Jul. 28, 2005

Related U.S. Application Data

(60) Provisional application No. 60/538,407, filed on Jan. 22, 2004.

(51) Int. Cl.
*A61B 18/20* (2006.01)
(52) U.S. Cl. .............................. 606/6; 606/4; 128/898
(58) Field of Classification Search ................ 606/4–6; 128/898
See application file for complete search history.

(56) References Cited

U.S. PATENT DOCUMENTS

| | | | |
|---|---|---|---|
| 2,134,152 A | 10/1938 | Schwarzmayr | |
| 3,828,788 A | 8/1974 | Krasnov et al. | |
| 4,391,275 A * | 7/1983 | Fankhauser et al. | 606/4 |
| 4,457,757 A | 7/1984 | Molteno | |
| 4,521,210 A | 6/1985 | Wong | |
| 4,558,698 A * | 12/1985 | O'Dell | 606/6 |
| 4,560,375 A | 12/1985 | Schulte et al. | |
| 4,604,087 A | 8/1986 | Joseph | |
| 4,633,866 A | 1/1987 | Peyman et al. | |
| 4,722,724 A | 2/1988 | Schocket | |
| 4,741,730 A | 5/1988 | Dormandy, Jr. et al. | |
| 4,791,927 A | 12/1988 | Menger | |
| 4,795,437 A | 1/1989 | Schulte et al. | |
| 4,846,172 A | 7/1989 | Berlin | |
| 4,850,955 A | 7/1989 | Newkirk | |
| 4,957,481 A | 9/1990 | Gatenby | |
| 5,053,006 A | 10/1991 | Watson | |
| 5,129,895 A | 7/1992 | Vassiliadis et al. | |
| 5,152,760 A | 10/1992 | Latina | |

(Continued)

FOREIGN PATENT DOCUMENTS

EP    1353340 A1    10/2003

(Continued)

OTHER PUBLICATIONS

PCT Search Report dated Jun. 19, 2006 of Patent Application No. PCT/US05/02118 filed Jan. 24, 2005.

*Primary Examiner*—A. Farah
(74) *Attorney, Agent, or Firm*—Vern Maine & Associates (57) ABSTRACT

Embodiments of the present invention provide a method and system of treating intraocular pressure. Laser light is directed to the ciliary region of the target eye. The light stimulates the ciliary region and ablates debris lodged therein. An immune response may be triggered by the stimulation of the ciliary body. Intraocular pressure is reduced by the increase in aqueous flow from the anterior chamber in the eye permitted by the resultant removal of debris blocking the uveo-scleral outflow pathway.

17 Claims, 10 Drawing Sheets

U.S. PATENT DOCUMENTS

| | | | |
|---|---|---|---|
| 5,169,395 A | 12/1992 | Narciso, Jr. | |
| 5,171,213 A | 12/1992 | Price, Jr. | |
| 5,222,952 A | 6/1993 | Loertscher | |
| 5,259,380 A | 11/1993 | Mendes et al. | |
| 5,292,362 A | 3/1994 | Bass et al. | |
| 5,346,464 A | 9/1994 | Camras | |
| 5,370,641 A | 12/1994 | O'Donnell, Jr. | |
| 5,372,595 A | 12/1994 | Gaasterland et al. | |
| 5,385,541 A | 1/1995 | Kirsch et al. | |
| 5,397,300 A | 3/1995 | Baerveldt et al. | |
| 5,411,473 A | 5/1995 | Ahmed | |
| 5,423,800 A * | 6/1995 | Ren et al. | 606/4 |
| 5,431,646 A | 7/1995 | Vassiliadis et al. | |
| 5,433,701 A | 7/1995 | Rubinstein | |
| 5,434,878 A | 7/1995 | Lawandy | |
| 5,454,796 A | 10/1995 | Krupin | |
| 5,465,737 A * | 11/1995 | Schachar | 128/898 |
| 5,520,621 A | 5/1996 | Edenbaum et al. | |
| 5,529,076 A * | 6/1996 | Schachar | 128/898 |
| 5,549,596 A | 8/1996 | Latina | |
| 5,549,598 A | 8/1996 | O'Donnell, Jr. | |
| 5,573,773 A | 11/1996 | Kis et al. | |
| 5,576,013 A | 11/1996 | Williams et al. | |
| 5,601,094 A | 2/1997 | Reiss | |
| 5,626,558 A | 5/1997 | Suson | |
| 5,688,264 A * | 11/1997 | Ren et al. | 606/15 |
| 5,704,907 A | 1/1998 | Nordquist et al. | |
| 5,707,986 A | 1/1998 | Miller et al. | |
| 5,709,653 A | 1/1998 | Leone | |
| 5,785,674 A | 7/1998 | Mateen | |
| 5,851,225 A | 12/1998 | Lawandy | |
| 5,865,831 A | 2/1999 | Cozean et al. | |
| 6,050,970 A | 4/2000 | Baerveldt | |
| 6,059,772 A | 5/2000 | Hsia et al. | |
| 6,241,721 B1 * | 6/2001 | Cozean et al. | 606/6 |
| 6,514,241 B1 | 2/2003 | Hsia et al. | |
| 6,682,523 B2 * | 1/2004 | Shadduck | 606/6 |
| 6,979,328 B2 * | 12/2005 | Baerveldt et al. | 606/41 |
| 6,989,007 B2 * | 1/2006 | Shadduck | 606/4 |

FOREIGN PATENT DOCUMENTS

| | | |
|---|---|---|
| JP | 200411332 | 4/2004 |
| WO | 8400101 A1 | 1/1984 |
| WO | 9409837 A1 | 5/1994 |
| WO | 9417755 A1 | 8/1994 |
| WO | 9721406 A1 | 6/1997 |
| WO | 0030592 | 6/2000 |
| WO | 0071019 A1 | 11/2000 |
| WO | 0103599 A2 | 1/2001 |
| WO | 2004/008945 A2 | 1/2004 |
| WO | 2004/091696 A1 | 10/2004 |

* cited by examiner

GLAUCOMA TREATMENT METHOD

RELATED APPLICATIONS

This application claims the benefit of U.S. Provisional Application No. 60/538,407, filed Jan. 22, 2004. This application is herein incorporated in its entirety by reference.

FIELD OF THE INVENTION

The present invention pertains to a treatment for glaucoma utilizing light energy to cause modification of tissue in the region of the angle of the anterior chamber to enhance aqueous outflows through the pathway of the uveoscleral plane to reduce intraocular pressure (IOP).

BACKGROUND OF THE INVENTION

Glaucoma is a major public health problem, affecting about two percent of the U.S. population. Numerous forms of glaucoma result in elevated intraocular pressure (IOP) in the eye, which can cause pathological changes in the optic nerve, and both central and peripheral visual field loss. If the IOP remains high for an extended period of time, total vision loss can occur. The elevated IOP is caused by an imbalance in fluid inflows and outflows in the eye, and the principal objective of medical treatment is the lowering of intraocular pressure.

The anterior chamber of the eye contains the aqueous humor (aqueous), a clear fluid that is produced continuously by the ciliary body around the lens. The constant flow of aqueous humor though the eye's front chamber exits through two different routes. One significant aqueous outflow pathway is through the trabecular meshwork and the Schlemm's canal. The trabecular meshwork is filtering structure that extends 360° around the circumference of the eye at the "angle"—the junction between the iris, sclera and cornea. The trabecular meshwork consists of layers of collagen webs that filter the outflows that reach Schlemm's canal. The meshwork has a monolayer of trabecular cells that produce enzymes for degrading extra-cellular material that may be captured by the filtering structure. Schlemm's canal is a passageway or series of septae that extend around the circumference of the eye adjacent to the meshwork. The aqueous fluid exits Schlemm's canal through a series of collecting channels that drain from the canal into the episcleral venous system.

The second aqueous outflow route is through the region of the ciliary body and the uveoscleral plane, wherein fluid migrates outwardly directly through tissue and between muscle fibers of the ciliary body.

In a normal eye, aqueous production by the ciliary body is equal to aqueous outflows to provide an IOP that remains constant in the 15 to 21 mm Hg range. In a patient suffering from glaucoma, the resistance through the outflow system is over about 21 mm Hg. In primary open angle glaucoma (POAG), the most common form of glaucoma, the principal resistance to fluid outflow is centered about the region of trabecular meshwork that is adjacent Schlemm's canal.

Numerous therapies have been developed for treating glaucoma by decreasing intraocular pressure. Pharmacological therapies include topical ophthalmic drops and oral medications that reduce the production of aqueous by the ciliary body or increase aqueous outflows via the uveoscleral route. However, drugs have occasional serious side effects, such as blurred vision, allergic reactions, headaches and potentially dangerous interactions with other drugs.

Surgical approaches for treating open-angle glaucoma consist of laser trabeculoplasty, trabeculectomy, and the implantation of aqueous shunts.

Trabeculectomy is a widely practiced surgery wherein microsurgical techniques are used to dissect the trabecular meshwork to allow more rapid aqueous outflow through the meshwork. Such procedures have proven to have limited long-term success. The dissection procedures often fail over time due to the body's wound healing response and resulting fibrosis that repairs and closes the dissected opening in the meshwork. After the dissections are healed up, the intraocular pressure again increases.

Implantable shunts and surgical methods are also known for providing a fluid path for aqueous humor to exit the anterior chamber of the eye to the sclera or a space beneath the conjunctiva.

Trabeculectomies and shunt surgeries and variations thereof have several disadvantages and moderate success rates. Such surgeries require significant surgical skills to create an incision through the full thickness of the sclera into the subconjunctival space. Further, the surgeries cause substantial trauma to the eye. The procedures are generally performed in an operating room and have a prolonged recovery time.

SUMMARY OF THE INVENTION

One embodiment of the present invention provides a method for treatment of intraocular pressure in a mammalian eye, that method comprising directing a laser light to a ciliary region of the eye, stimulating the ciliary region, and ablating debris lodged in the ciliary region.

Another embodiment of the present invention provides such a method wherein that laser light has a depth penetration not less than 50 µm.

A further embodiment of the present invention provides such a method wherein that laser light has a depth penetration not less than 70 µm.

Yet another embodiment of the present invention provides such a method wherein that laser light has a depth penetration not less than 200 µm.

A yet further embodiment of the present invention provides such a method further comprising targeting a ciliary trabeculum of the ciliary region with the laser light.

Even another embodiment of the present invention provides such a method further comprising evoking an immune response.

An even further embodiment of the present invention provides such a method wherein the immune response comprises the activation of cytokines and macrophages.

Still another embodiment of the present invention provides such a method further comprising goniscopically applying the laser light to the ciliary trabeculum.

A still further embodiment of the present invention provides such a method further comprising targeting a ciliary body disposed within the ciliary region.

One embodiment of the present invention provides such a method further comprising evoking an immune response.

Another embodiment of the present invention provides such a method wherein the immune response comprises the activation of cytokines and macrophages.

A further embodiment of the present invention provides such a method further comprising compressing a sclera of the eye with a laser delivery device.

Yet another embodiment of the present invention provides such a method further comprising transmitting the laser light through a sclera of the eye.

A yet further embodiment of the present invention provides such a method further comprising treating a plurality of points on the sclera.

Even another embodiment of the present invention provides such a method wherein the laser light has a wavelength greater than 600 nm.

An even further embodiment of the present invention provides such a method wherein the laser light has a wavelength in the range of 700 nm to 1000 nm.

Still another embodiment of the present invention provides such a method wherein the laser light is generated by a titanium sapphire laser.

One embodiment of the present invention provides a system for the treatment of intraocular pressure in mammalian eyes, that system comprising, a laser generator producing a laser light having a tissue penetration range of greater that 50 µm; and a laser delivery device coupled to the laser, whereby the laser light targets a ciliary body of the eye.

Another embodiment of the present invention provides such a system further comprising a contact ring disposed around an anterior chamber of the eye whereby the laser light is delivered to a plurality of target points simultaneously.

A further embodiment of the present invention provides such a system wherein the device is configured to directly contact a sclera of the eye.

One embodiment of the present invention provides a method for trans-scleral ciliaryplasty, the method comprising, compressing a sclera of a patient's eye proximal to a ciliary region of the eye; directing a beam of laser light through the sclera into the ciliary region; and initiating an immune response.

Another embodiment of the present invention provides such a method where the laser has a wavelength in the range of 700 nm to 1000 nm.

A further embodiment of the present invention provides such a method wherein the laser is a titanium sapphire laser.

Yet another embodiment of the present invention provides such a method wherein the immune response comprises excitation of cytokines and macrophages.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION OF THE INVENTION

Figure 1:
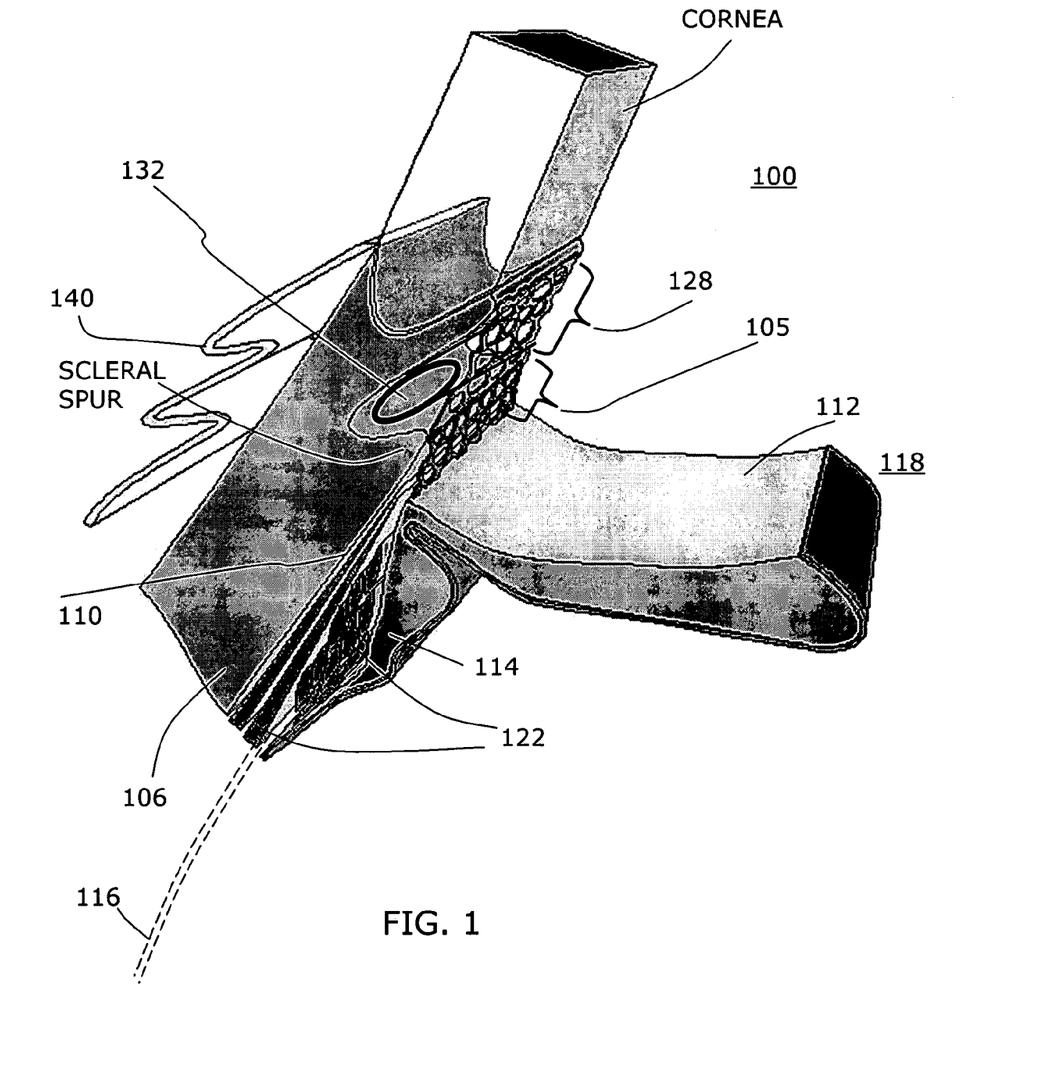
FIG. 1 is a schematic view of the anatomy of a patient's eye showing the region of the uveo-scleral plane.

FIG. 1 illustrates the anatomy about the anterior chamber 100 of a human eye. The present invention relates to means to enhance aqueous outflows from the anterior chamber 100 by applying energy to a targeted tissue region 105 within a narrow plane at the periphery of the anterior chamber. The anterior chamber of the eye contains the aqueous humor, a clear fluid that is produced continuously by the ciliary body. The constant flow of aqueous humor though the eye's front chamber exits through two different routes: (i) the corneo-scleral trabeculum and Schlemm's canal, and (ii) the uveoscleral route.

It has been found that light-mediated treatments of tissue about the uveoscleral route can enhance outflows. The targeted tissue in about the interface of uvea and sclera 106, and is described at times herein as the uveal-iris strands 105 (FIG. 1). The targeted tissue region 105 transitions into the uveo-scleral plane indicated at 110 in FIG. 1. The uvea of the eye consists collectively of the iris 112, the ciliary body 114 and the choroid 116. The iris in FIG. 1 is the curtain of the eye that surrounds the pupil 118. The ciliary body 114 is the body of tissue that connects the iris with the choroid 116 and includes a group of ciliary muscles 122 which act on the lens (not shown) of the eye to change its shape. The choroid 116 of the eye is the thin vascular middle layer of the eye that is situated between the sclera (white of the eye) 106 and the retina, the nerve layer that lines the back of the eye.

Figure 2:
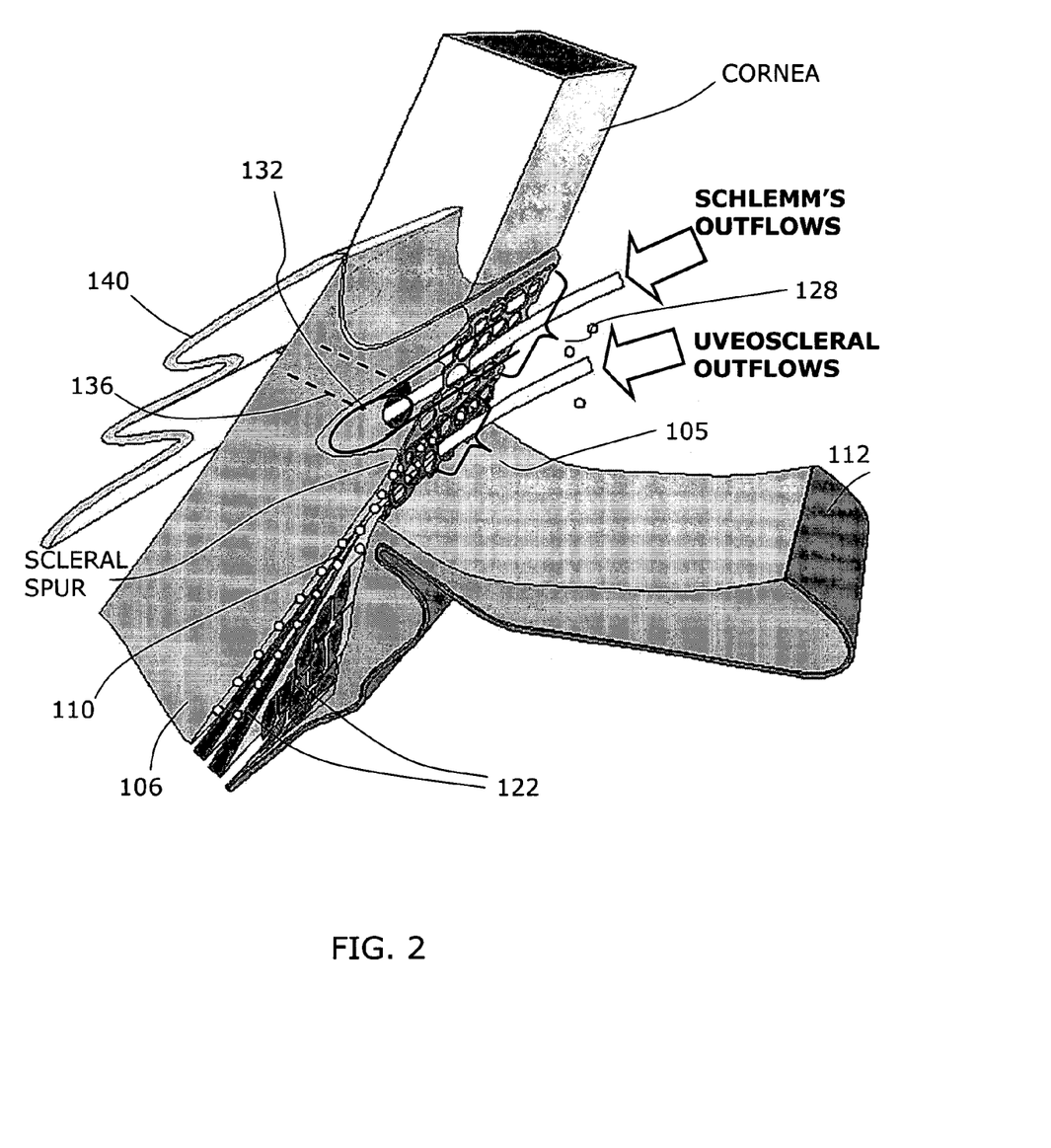
FIG. 2 is a schematic view similar to FIG. 1 illustrating the two paths of aqueous outflows from the anterior chamber.

As described above, there is a significant aqueous outflow route through the region of the ciliary body 104 and uveoscleral plane 110, wherein fluid migrates outwardly from the anterior chamber 100 directly through tissue and between muscle fibers 122 of the ciliary body. There is no substantial tissue barrier between the anterior chamber 100 and the ciliary muscles 122. Thus, there is no membrane or barrier to prevent aqueous from passing into and between the muscle bundles 122 into the suprachoroidal space (or uveoscleral plane 110). The region at the periphery of the anterior chamber does contain a fiber or tissue region described herein as uveal-iris strands 105 (or ciliary trabeculum) at the outermost periphery of the iris 112 (see FIGS. 1-2). FIG. 2 illustrates the uveoscleral outflow path through the iris strand tissue region 105 and the ciliary muscle bundles 122. As used herein, the term "uveoscleral outflows" describes aqueous outflows that exit the anterior chamber 100 through tissue posterior to the corneo-scleral trabeculum (trabecular meshwork) 128 and Schlemm's canal 132 (see FIG. 1). In other words, the aqueous flows through the ciliary muscle bundles 122, through the periphery of the iris 112, and generally through the uveal-iris strands 105 to the uveoscleral plane 110. Thereafter, it is believed that the aqueous can pass into the venous system and migrate into or through the sclera. The vessels of the choroid 116 and ciliary processes 114 (FIG. 1) are highly permeable, and the protein concentration in the extravascular space of the uvea is thus unusually high. These proteins can exit the interior of the eye through the sclera (albumin).

Figure 3:
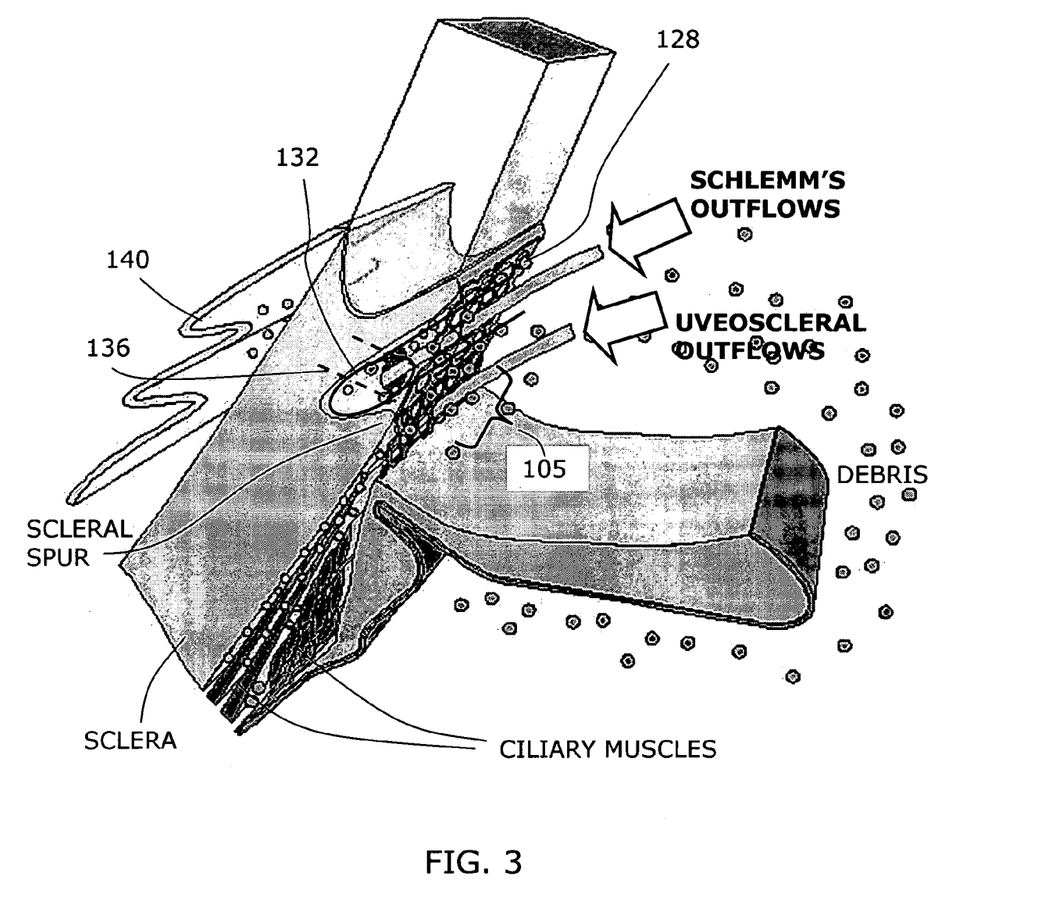
FIG. 3 is an exploded view of FIG. 2 illustrating the two paths of aqueous outflows from the anterior chamber.

FIG. 3 also illustrates the other primary aqueous outflow path through the corneo-scleral trabeculum 128 and Schlemm's canal 132. After the aqueous humor reaches and Schlemm's canal 132, which may be a series of septae rather than a true 3600 canal, the outflows further pass through collectors 136 that extend outwardly and pass fluid to the episcleral venous system at the interior of the conjunctiva 140. In FIGS. 2-3 and elsewhere in this disclosure, these aqueous flows are described as "Schlemm's outflows".

The exploded view of FIG. 3 provides a better view of the two distinct flow paths for aqueous to exit the anterior chamber 100.

Figure 4:
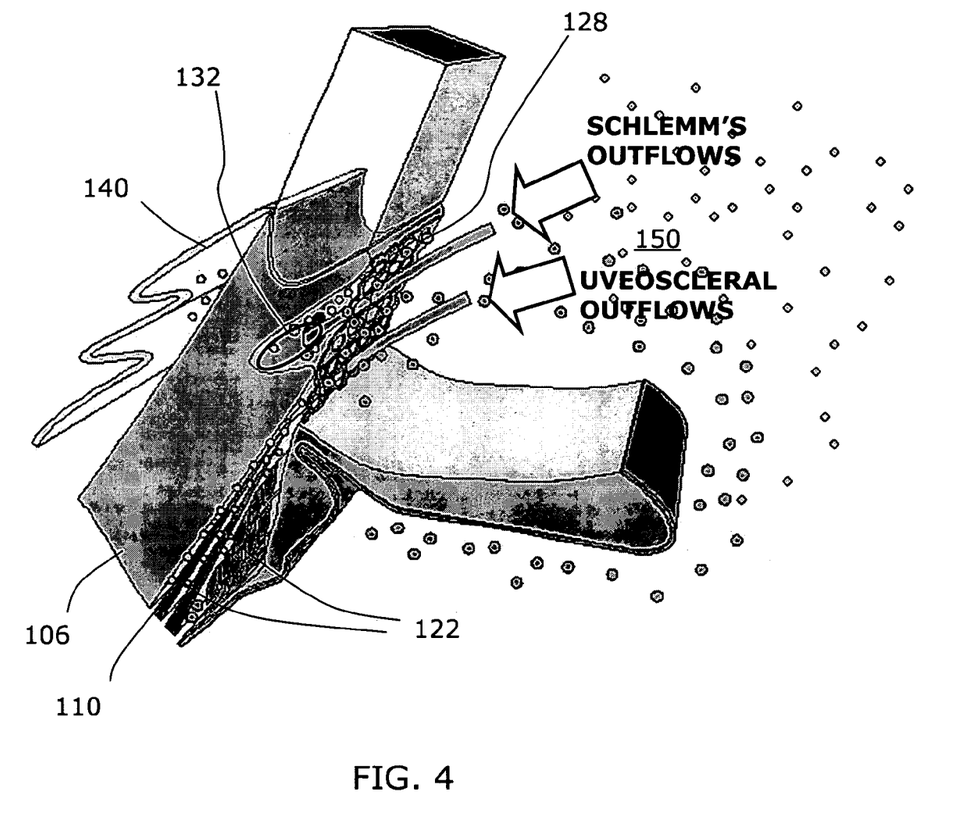
FIG. 4 is schematic view of a young eye.

FIG. 4 depicts a young, healthy eye wherein pigment (e.g., from lens and iris) and other cellular debris 150 circulate in the anterior chamber 100 and naturally exit together with aqueous through the uveoscleral outflows and Schlemm's outflows.

Figure 5:
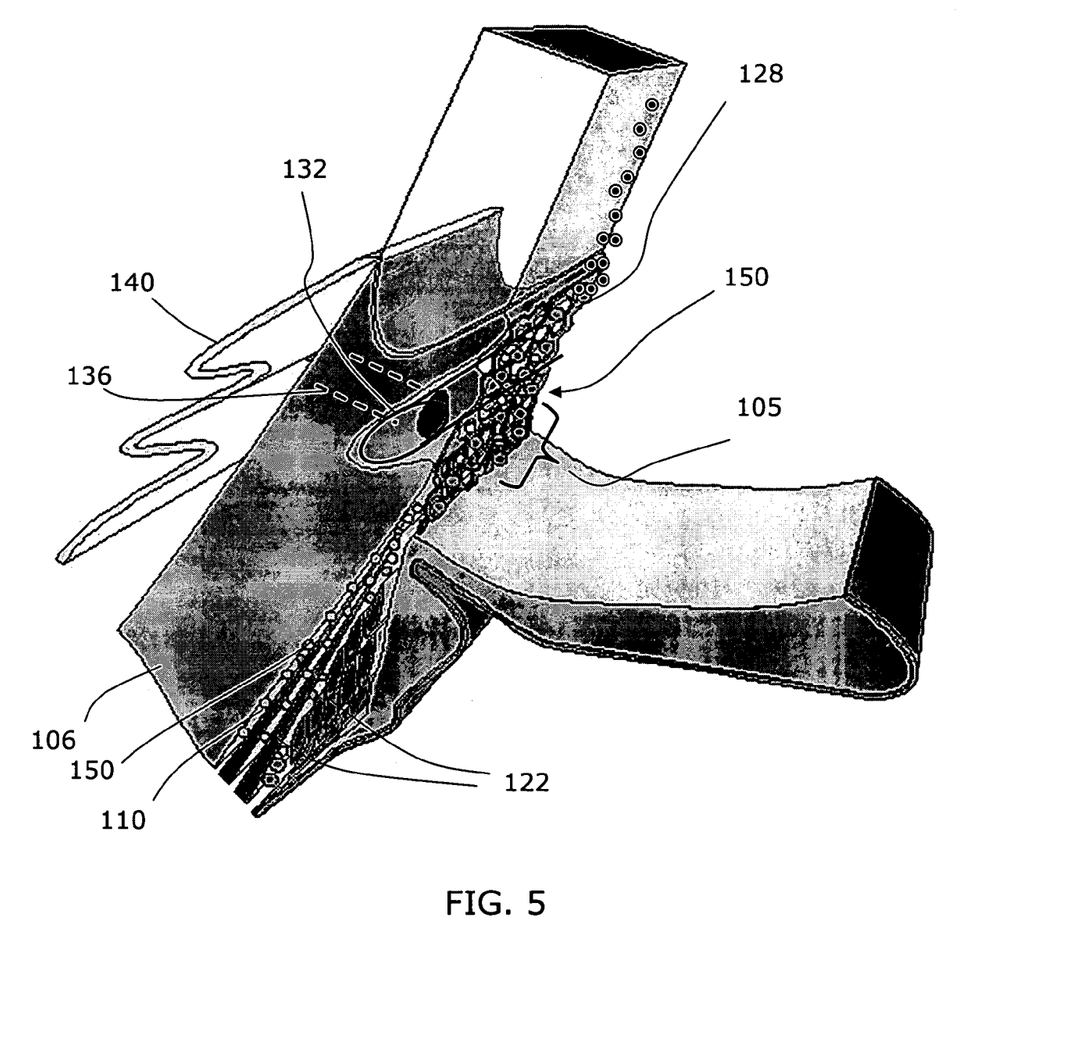
FIG. 5 is view of a old, glaucomatous eye with debris and plaque in the uveoscleral outflow pathway.

The author has performed comparative morphological studies of young and older glaucomatous eyes. As was to be expected, the studies revealed an increase in extra-cellular material in the sub-endothelial region of the Schlemm's canal in the older glaucomatous eyes. Of particular interest, the author also found a significant increase in the extra-cellular material in the outflow pathways of the uveoscleral plane 100 and ciliary muscle bundles 122. In some of the studies, it appears that a type of plaque is built up within the tissue of the uveoscleral outflow route. FIG. 5 is a graphic depiction of debris 150 as it accumulates in an older glaucomatous eye.

Figure 7:
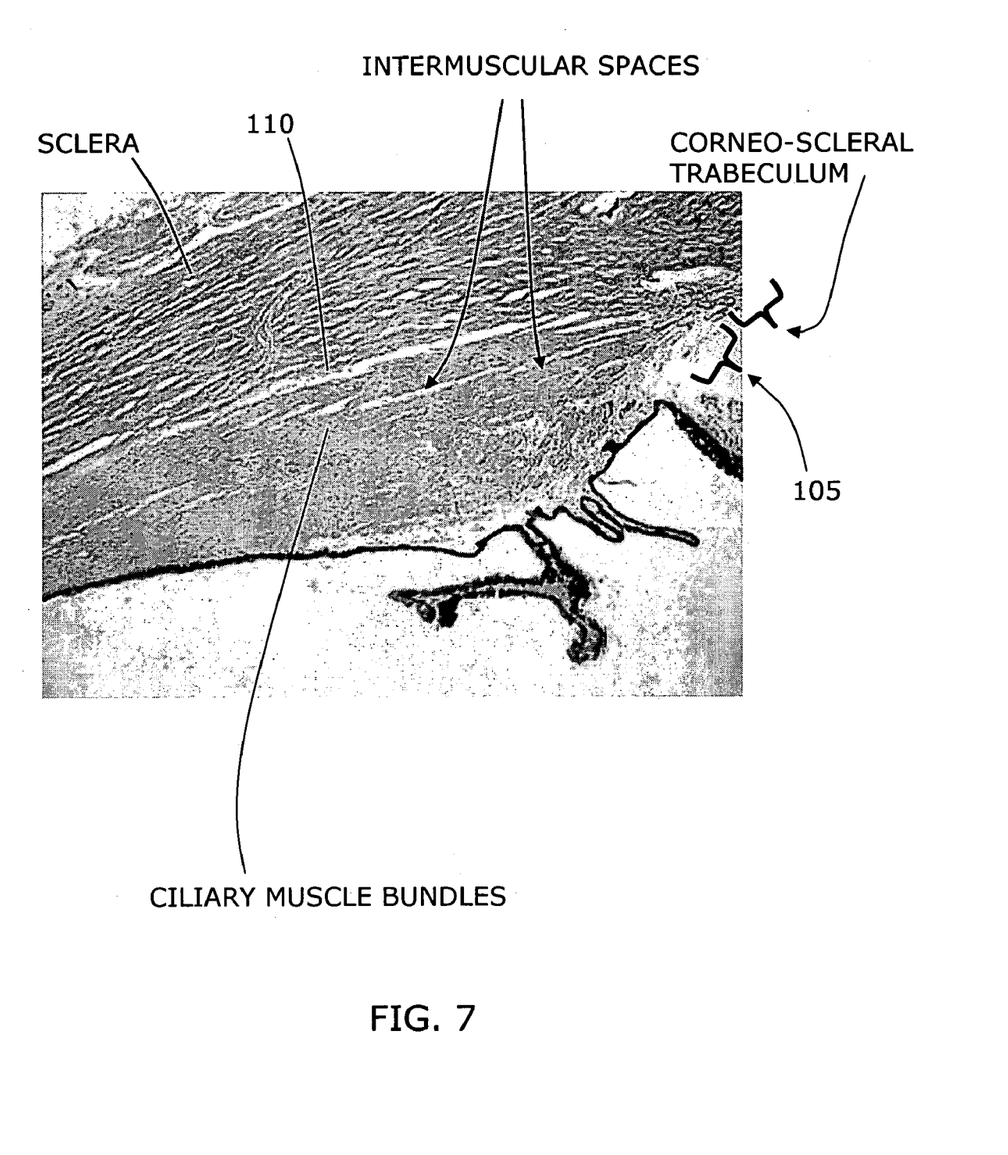
FIG. 7 is an image of a young human eye showing flow spaces with ciliary muscle bundles.
Figure 8:
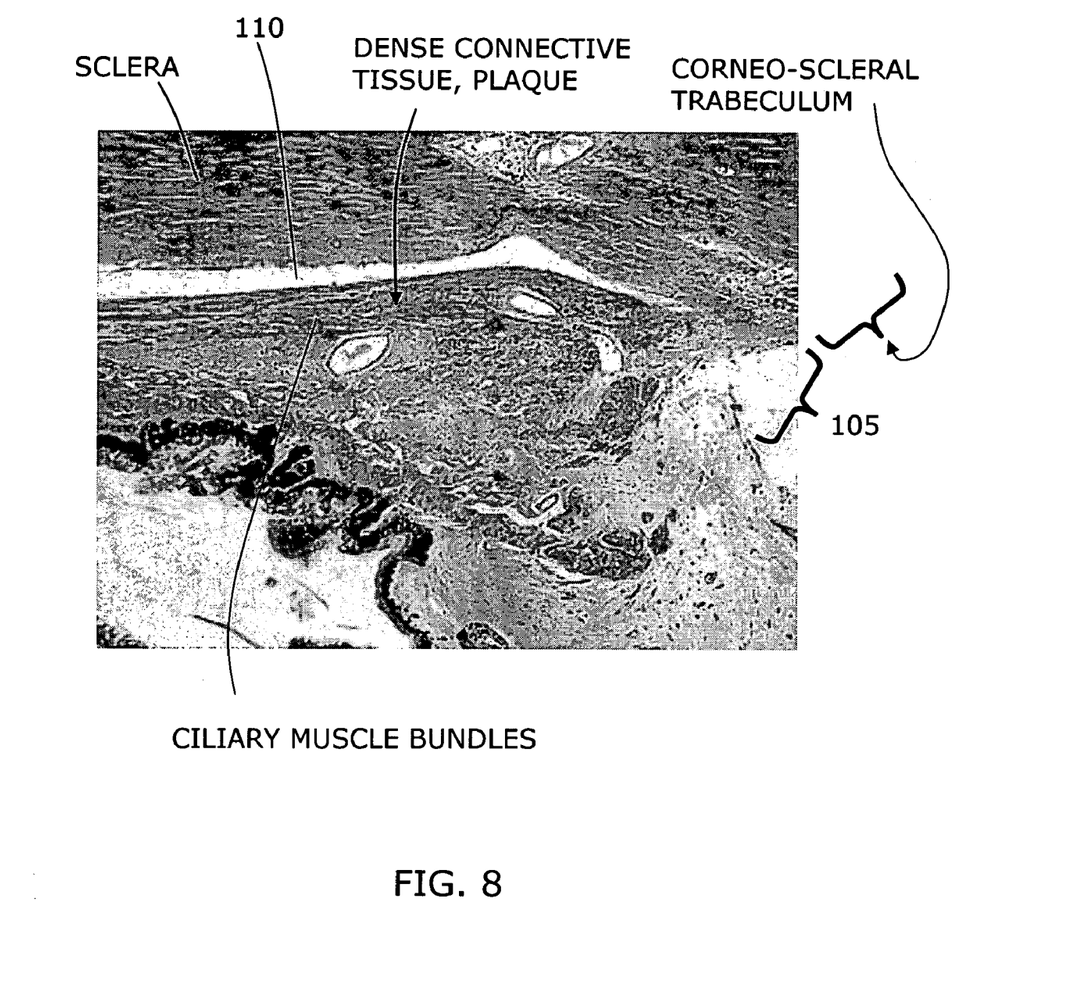
FIG. 8 is an image of a old, glaucomatous eye with plaque and dense connective tissue in the uveoscleral outflow pathway.

FIGS. 7 and 8 are images of a young human eye and an older glaucomatous human eye, respectively, which correspond to the schematic representations of FIGS. 4 and 5. In the image of FIG. 7, the young eye has substantial inter-muscular spaces that allow for fluid outflows. In the image of the glaucomatous eye in FIG. 8, there is dense connective tissue, and plaque-like materials that are believed to result from cellular debris build-up and the wound healing response that causes connective tissue growth.

Figure 6:
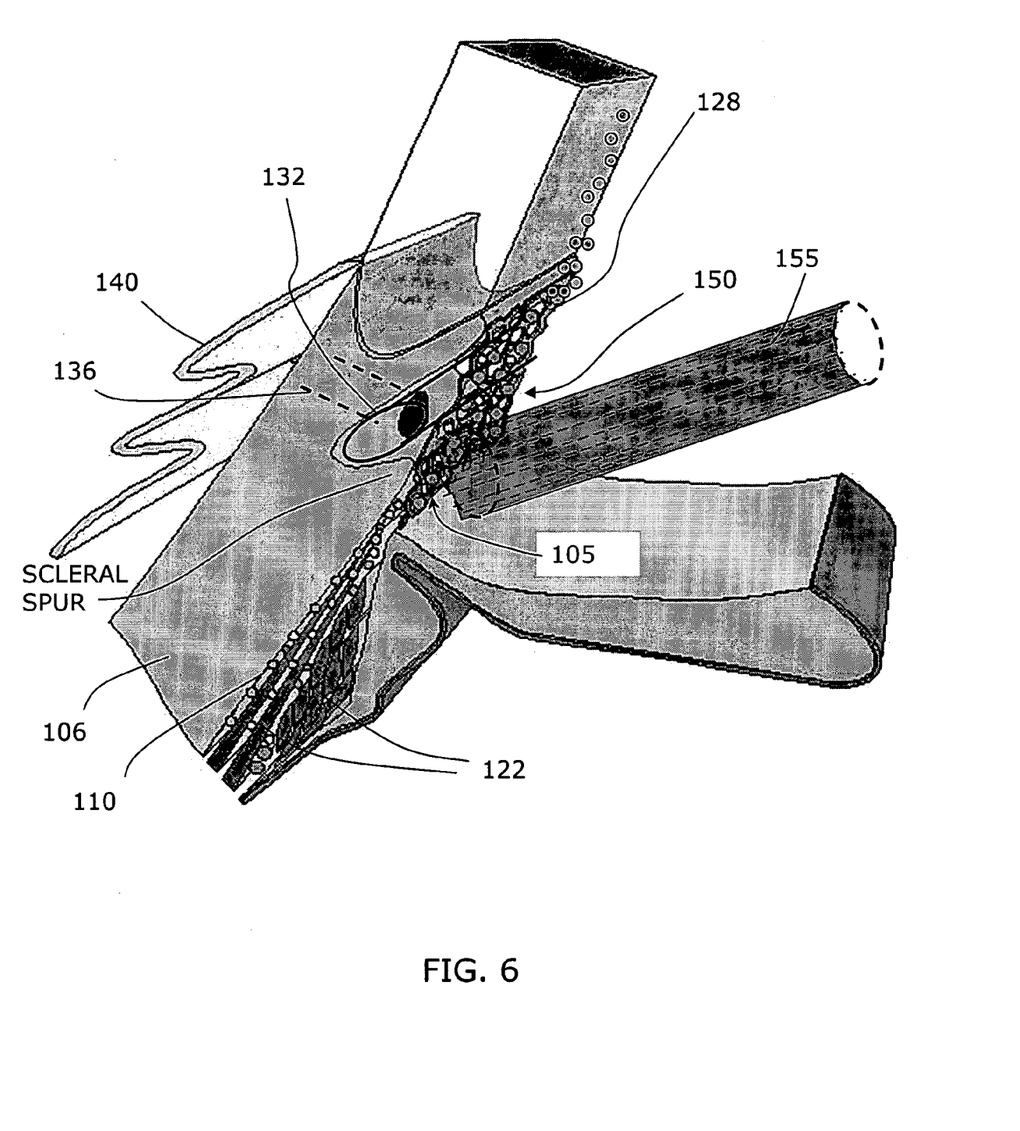
FIG. 6 is a view of the method of the invention illustrating laser irradiation of the tissue region about the uveo-scleral interface exposed to the anterior chamber.

In one embodiment of the present invention applied to an animal model, as illustrated in FIG. 6., laser irradiation about the junction (tissue region 105 in FIGS. 1-8) of the uvea and sclera posterior of the corneo-sclera trabeculum 128, herein more described as uveal-iris strands or ciliary trabeculum tissue 105, resulted in enhanced outflows through the uveoscleral route.

One embodiment of the present invention relies on the application of energy via laser irradiation to the uveal-iris strands 105, the peripheral iris and generally to the uveo-scleral interface 110 that is exposed to the anterior chamber which enhances aqueous flows through the "uveoscleral outflow" route as illustrated in FIGS. 2 and 3.

One embodiment of the present invention comprises an alternative method of using laser irradiation to apply energy to the region of uveal-iris strand tissue 105 or ciliary trabeculum, as shown in FIG. 6, about the uveo-scleral junction exposed to the anterior chamber 100. The laser energy is applies gonioscopically, as is known in the art, and can be in a 360° band or in any smaller angular region. It has been found that the energy delivery parameters below can cause a modification of tissue, and increased fluid permeability and outflows within the tissue region 105. According to various embodiments, the modification may be bioshock, microvibration, shortbioshock, bioultrashock, photocavitation, microcavitation, shock wave, or thermal effects.

In one embodiment of the present invention, the laser radiation has a wavelength between 400 and 1550 nanometers, and more preferably between 750 and 1000 nanometers. The method utilizes an energy level per laser pulse ranging from 1 to 500 millijoules (mJ), and more preferably an energy level ranging from 10 to 250 millijoules per pulse. The method uses a laser pulse duration of ranging between 1 and 50 microseconds, and more preferably the pulse duration ranges between 5 and 25 microseconds. The method used a laser spot size ranging between about 50 and 200 microns. One suitable laser source can be a Ti:Sapphire laser of the type that produces a wavelength in the range of 785-795 nm.

In one embodiment of the present invention a method of stimulating the ciliary region is provided where coherent light is directed to the ciliary body 114 and uveoloscleral outflow pathway. Such stimulation excites a biological response, in one embodiment this biological response comprises a recruitment of macrophages and cytokines. Coherent light may be introduced either by directing a beam of such light through the anterior chamber of the eye 100 to the ciliary trabeculum or with a trans-scleral beam directed to the ciliary body. In one embodiment, the coherent light is provided by a titanium sapphire laser having a wavelength of 790 nm. One skilled in the art will readily appreciate that other lasers having suitable effective tissue penetration would also be within the scope of the present invention.

In one embodiment wherein the light is directed through the anterior chamber of the eye, laser light may be directed into the anterior chamber 100, and focused proximally to the ciliary trabeculum 105. In one such embodiment, it is desirable that the focal point of the laser be disposed in the ciliary region defined by the uveoscleral outflow pathway, ciliary body and ciliary trabeculum. According to such an embodiment, the light may be delivered using a goniolens or other suitable tool for viewing and direction of light towards the angle of the anterior chamber.

Figure 9:
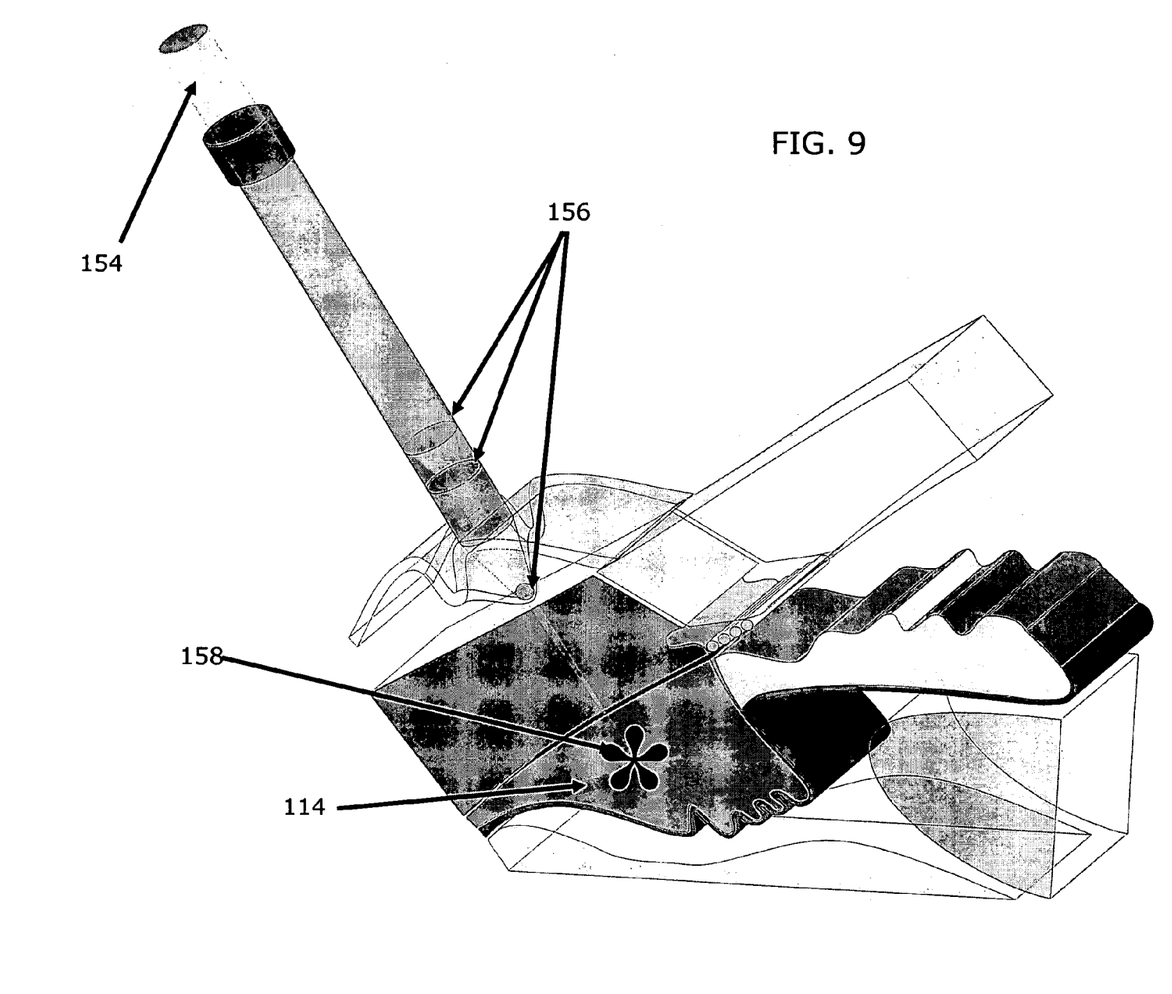
FIG. 9 is a partial cross sectional elevation view of a human eye illustrating a trans-scleral ciliaryplasty according to one embodiment of the present invention.
Figure 10:
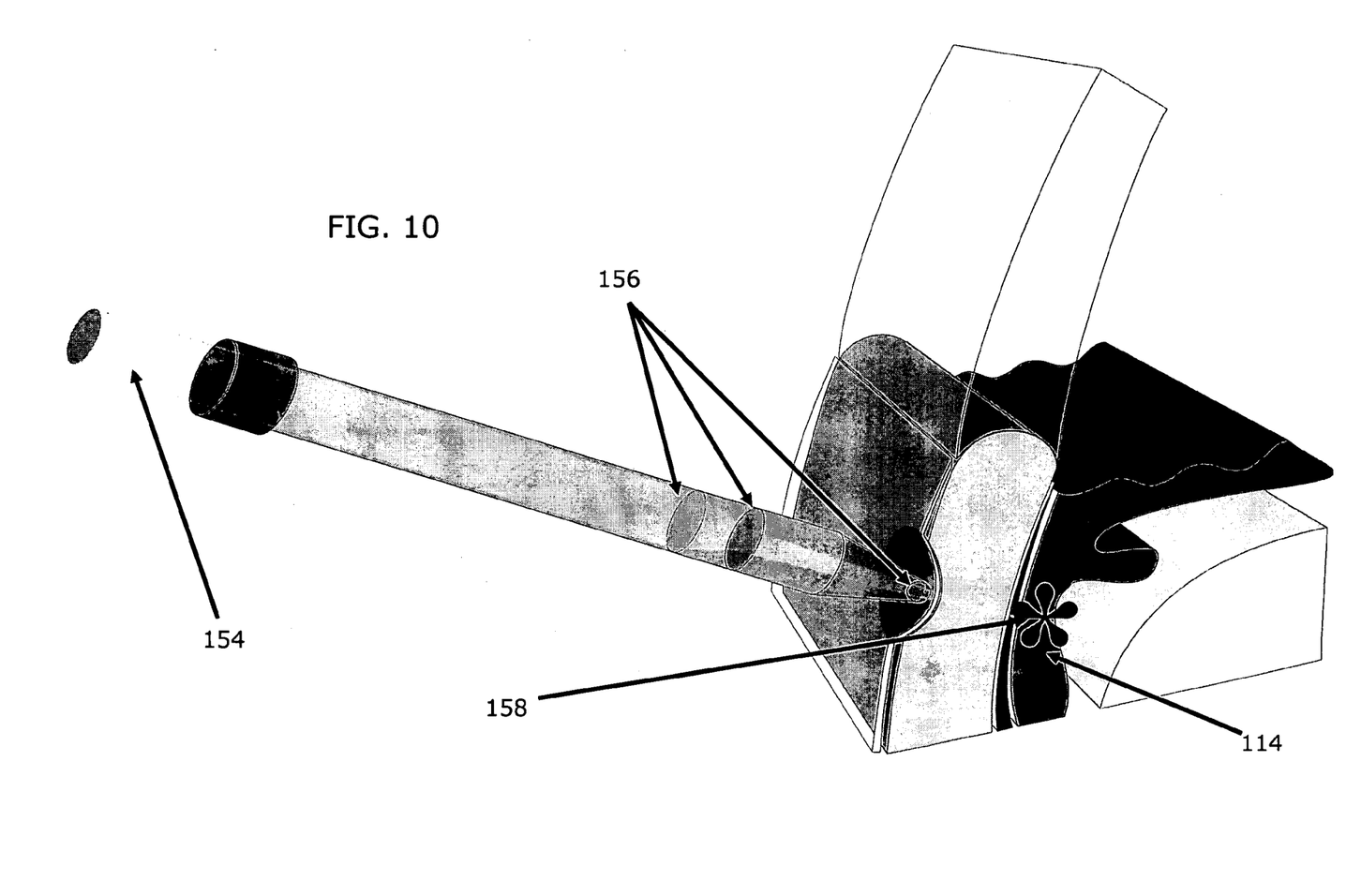
FIG. 10 is a partial cross sectional elevation view of a human eye illustrating a trans-scleral ciliaryplasty according to one embodiment of the present invention.

Alternatively, illustrated in FIG. 9 and FIG. 10, coherent light may be directed into the ciliary body 114 through the sclera. Application of pressure to the sclera causes the sclera to become transparent to light of certain wavelengths. This characteristic of the sclera allows the passage of laser light through the sclera when the sclera is compressed by the application of a probe or other light delivery device. By the application of a laser probe or other coherent light delivery device to the exterior of the sclera, coherent light may be delivered to the ciliary region directly through the exterior of the eye. In such embodiments, the coherent light will typically be selected from light sources that permit a penetration of about approximately 200 μm. In one embodiment, a laser having a wavelength of 790 nm is employed. For such an embodiment to prompt the correct response, the penetration depth must be greater than the thickness of the structures disposed between the exterior of the sclera and the target region.

In such an embodiment, light may be delivered by pen or pencil like probes manipulated by a user. The probe may comprise a fiber optic light delivery channel and an array of lenses or mirrors whereby the light is focused on a target region. In one embodiment, a lens of the array 156 is disposed at the end on the probe, and when in use, placed in contact with the sclera of the subject eye. The user may then select one or more positions around the cornea for trans-scleral ciliaryplasty. Alternatively, the laser may be simultaneously directed via a plurality of lenses disposed in a ring around the cornea to pre-selected sites disposed on the sclera around the cornea.

In such embodiments both the biological effect and the ablation or removal of detritus and other debris clogging the ciliary trabeculum and uveoscleral outflow pathway would contribute to the improvement in flow, thereby decreasing elevated intraocular pressure. The effects of phagocytes, macrophages and cytokines are well understood by those skilled in the biological sciences. The laser ciliaryplasty effectively stimulates the body's immune response and prompts the body to remove the debris. The removal of the debris allows for greater flow of aqueous, and consequently, a decrease in intraocular pressure.

In one embodiment, the target region may be exposed to light pulses of at least 5 μsec. In other embodiments this pulse may be 7 μsec or upwards of 20 μsec. One skilled in the art will appreciate that different exposure times will elicit different biological reactions.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto

What is claimed is:

1. A method for the therapeutic reduction of intraocular pressure in a mammalian eye, said method comprising:
    Directing a laser light from a laser delivery device external to said eye to a ciliary region of said eye; said laser light being selected to ablate debris within said ciliary region without destruction of surrounding tissues,
    Stimulating said ciliary region;
    Ablating debris lodged in said ciliary region without perforation of tissues of said eye within said ciliary region.

2. The method according to claim 1 wherein said laser light has a depth penetration not less than 50 μm.

3. The method according to claim 1 wherein said laser light has a depth penetration not less than 70 μm.

4. The method according to claim 1 wherein said laser light has a depth penetration not less than 200 μm.

5. The method according to claim 1, further comprising targeting a ciliary trabeculum of said ciliary region with said laser light.

6. The method according to claim 5 further comprising evoking an immune response.

7. The method according to claim 6 wherein said immune response comprises the activation of cytokines and macrophages.

8. The method according to claim 5 further comprising goniscopically applying said laser light to said ciliary trabeculum.

9. The method according to claim 1 further comprising targeting a ciliary body disposed within said ciliary region.

10. The method according to claim 9 further comprising evoking an immune response.

11. The method according to claim 10 wherein said immune response comprises the activation of cytokines and macrophages.

12. The method according to claim 9 further comprising compressing a sclera of said eye with said laser delivery device.

13. The method according to claim 9 further comprising transmitting said laser light through a sclera of said eye without a substantial effect on said sclera.

14. The method according to claim 13 further comprising treating a plurality of points on said sclera.

15. The method according to claim 1 wherein said laser light has a wavelength greater than 600 nm.

16. The method according to claim 1 wherein said laser light has a wavelength in the range of 700 nm to 1000 nm.

17. The method according to claim 1 wherein said laser light is generated by a titanium sapphire laser.

* * * * *